United States Patent [19]

O'Donnell

[11] Patent Number: 5,217,452
[45] Date of Patent: Jun. 8, 1993

[54] TRANSSCLERAL LASER TREATMENT OF SUBRETINAL NEOVASCULARIZATION

[76] Inventor: Francis E. O'Donnell, 709 The Hamptons La., St. Louis, Mo. 63017

[21] Appl. No.: 884,008

[22] Filed: May 18, 1992

[51] Int. Cl.$^5$ ............................................. A61F 9/00
[52] U.S. Cl. .................................... 606/4; 128/898
[58] Field of Search ............................... 128/897–899; 606/4–6, 15–18

[56] References Cited

U.S. PATENT DOCUMENTS

| | | |
|---|---|---|
| 4,592,353 | 6/1986 | Daikuzono . |
| 4,693,244 | 9/1987 | Daikuzono . |
| 4,736,743 | 4/1988 | Daikuzono . |
| 4,785,805 | 11/1988 | Joffe et al. . |
| 4,895,144 | 1/1990 | Cook et al. . |
| 4,895,145 | 1/1990 | Joffe et al. . |
| 5,067,951 | 11/1991 | Greve .................................. 606/4 |
| 5,147,349 | 9/1992 | Johnson et al. ..................... 606/4 |

Primary Examiner—Kyle L. Howell
Assistant Examiner—John P. Locyk
Attorney, Agent, or Firm—Paul M. Denk

[57] ABSTRACT

A method of treating subretinal neovascularization (SRNV) using a fiberoptic probe to introduce laser energy transsclerally to obliterate the SRNV complex without damaging the sclera or retina.

12 Claims, 3 Drawing Sheets

TRANSSCLERAL LASER TREATMENT OF SUBRETINAL NEOVASCULARIZATION

BACKGROUND OF THE INVENTION

This invention relates to a method of performing laser ophthamological surgery, more specifically to a technique for treating subretinal neovascularization (SRNV) with transscleral laser therapy.

The human eyeball is shown generally at 1 in FIG. 1. Subretinal neovascularization (SRNV) 6 is a growth of new blood vessels underneath the retina 3 and above the choroid 4 (See FIGS. 1 and 2). New blood vessels originating in the inner layer of choroid 4 develop between the choroid 4 and retina 3 with capillaries eventually invading retina 3 causing macular changes, degeneration, myopia, and eventually vision loss. New blood vessels growing between the pigment area of retina 3 and the sensory area of the retina 3 can hemorrhage leading to development of fibrous tissue in the retina resulting in visual impairment and even blindness. Serous exudate and fibrosis can also lead to the formation of a scar, degeneration of the retinal photoreceptors, and atrophy of the nearby retina 3 and choroid 4.

The exact reason for the vascular proliferation is unknown. Experiments have shown that the new vessels extend by proliferation of endothelial cells and pericytes, along with macrophages and actively proliferating epithelial cells.

To date there is no known pharmacological means for inhibiting or retarding the vessel proliferation. Traditional laser photocoagulation has been shown to be effective in selected cases of vasoproliferation. Argon and krypton laser photocoagulation has been most effective with most reported radomized trials using the argon blue/green laser. Krypton red lasers are also widely available, however, krypton red cannot penetrate intraretinal hemorrhage without producing inner retinal damage.

The object of photocoagulation is to use laser energy to obliterate the neovascular complex. Generally, intense photo coagulation is extended at least 100 microns beyond the parameter of the neovascular complex if the complex is more than 300 microns from the center of the retina. Once neovascularization starts, the entire membrane must be effectively photocoagulated because partial coagulation stimulates proliferation of additional blood vessels.

FIGS. 3-5 illustrate prior art techniques for performing photocoagulation. FIG. 3 illustrates a laser delivery system mounted on a slit lamp, known in the art, shown generally at 11. The laser energy generator 13 is connected to laser L via fiber optic cables 14 at laser input 15. FIG. 4 illustrates the device of FIG. 3 in use. A surgeon S seated at slit lamp 11 with a laser L is mounted on slit lamp 11 and patient P is opposite surgeon S. Surgeon S visualizes the treatment area through the slit lamp 11, activates laser L and laser energy E is delivered through the air (non-contact) and into the patient's eye. According to FIG. 5, the energy beam E travels through cornea 16 at lens 18 to the subretinal neovascularization complex 6. Laser beam E must go through retina 3 to reach the subretinal neovascular complex 6. This risks severe damage to the retina, i.e., iatrogenic loss of vision.

SUMMARY OF THE INVENTION

It is, therefore, an object of the method of the present invention to provide laser obliteration of subretinal neovascularization SRNV that avoids introduction of laser energy through the retina.

Another object of the invention is to provide transscleral photocoagulation of the subretinal neovascularization complex.

Still another object of the invention is to provide a method for treating SRNV that employs a curved, fiberoptic probe that allows transsceleral contact treatment of the SRNV through the posterior sclera.

Yet another object of the invention is to provide a method of transscleral treatment of SRNV using an energy wave length that is transmitted by the sclera (e.g. 1064 NM) and choroid through a fiberoptic delivery system.

Another object of the invention is to provide a method for transscleral treatment of SRNV that is safe and easy to perform, does not require hospitalization, lessens the risk of untoward reactions and complications, and provides ablation of the disease process.

Other objects of the method of the present invention will become obvious to those skilled in the art upon review of the accompanying drawings and description of the preferred embodiment.

Briefly stated, a method of treating subretinal neovascularization using a fiberoptic instrument to introduce laser energy transsclerally to obliterate the SRNV complex without causing damage to the retina. The surgeon introduces the fiberoptic probe placing the tip of the probe against the sclera at the point of the SRNV complex. The tip of the probe focuses laser energy at the SRNV and avoids damage to the sclera and to the retina.

DESCRIPTION OF THE PREFERRED EMBODIMENT

Figure 1:
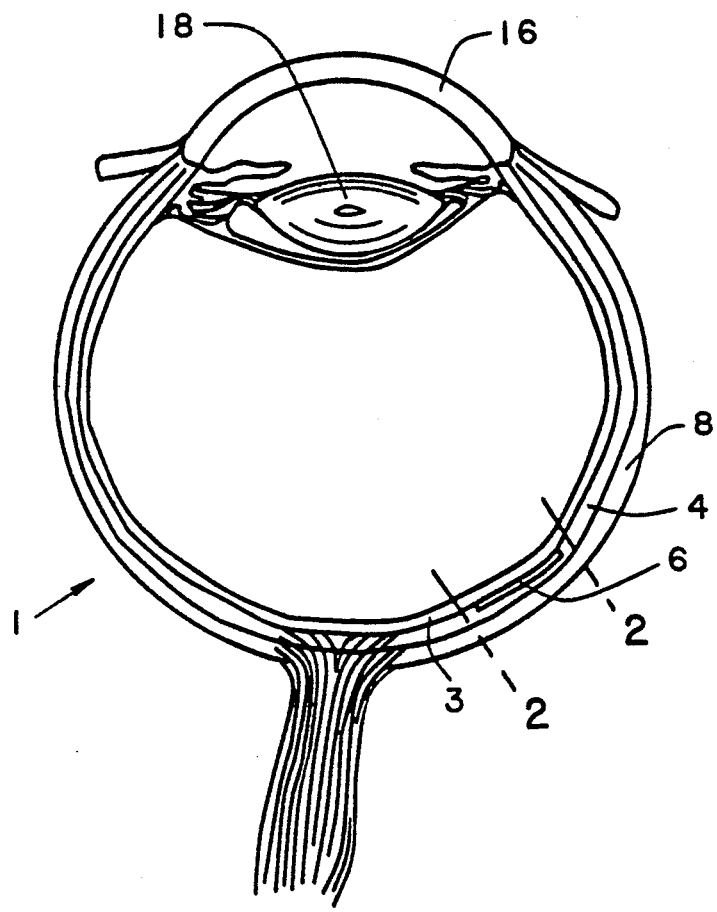
FIG. 1 is a cross-section view of the human eyeball.
Figure 2:
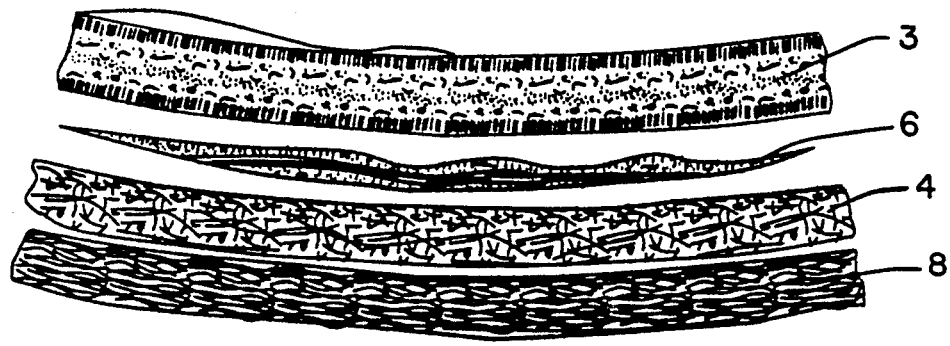
FIG. 2 is a cross-sectional view of the outer covering of the human eyeball taken along lines 2—2 of FIG. 1 demonstrating subretinal neovascular disease.
Figure 3:
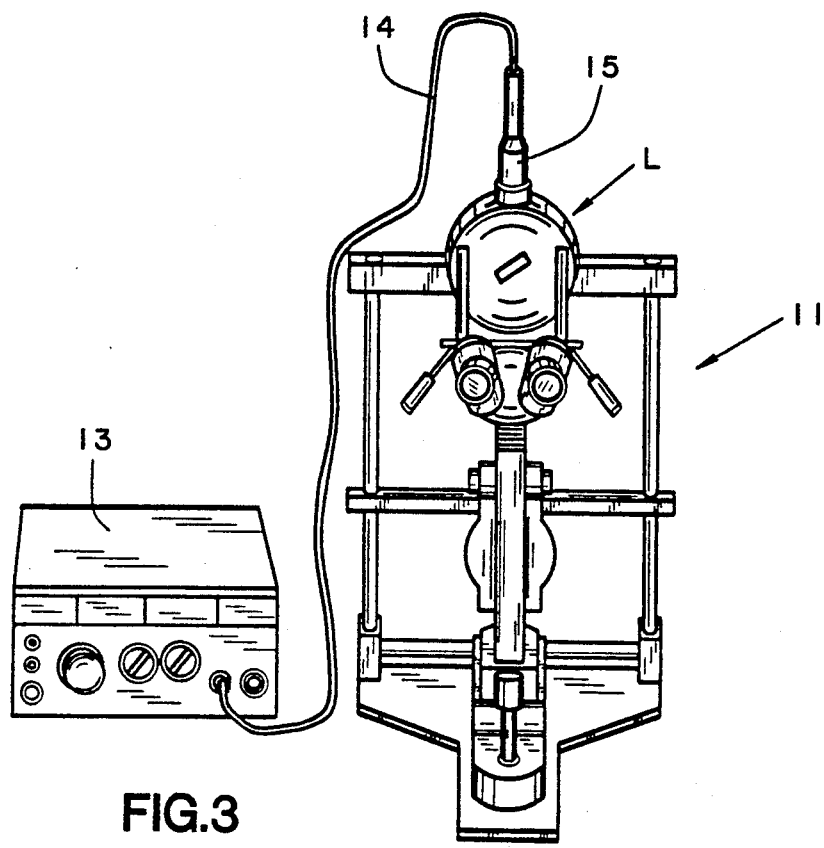
FIG. 3 is a perspective view of a laser delivery system mounted on a slit lamp of the traditional type.
Figure 4:
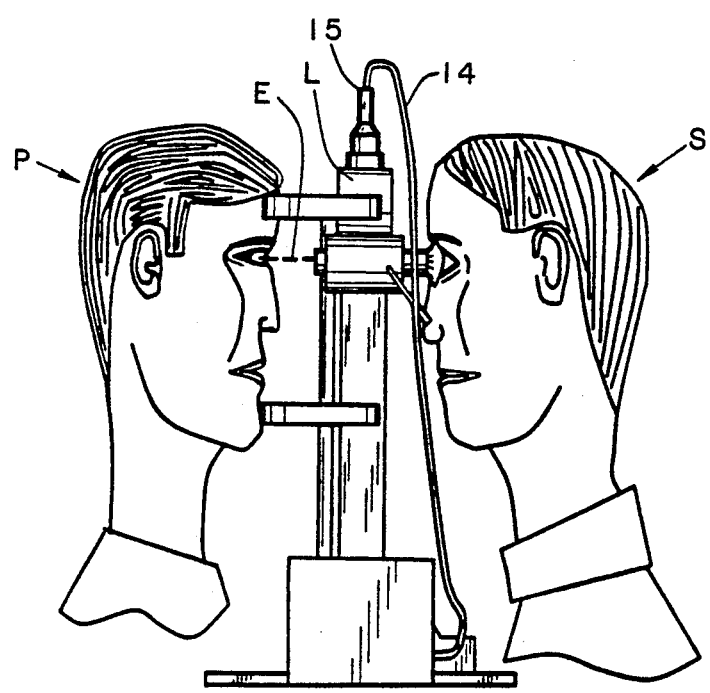
FIG. 4 is an isometric view of the instrument of FIG. 3 in use.
Figure 5:
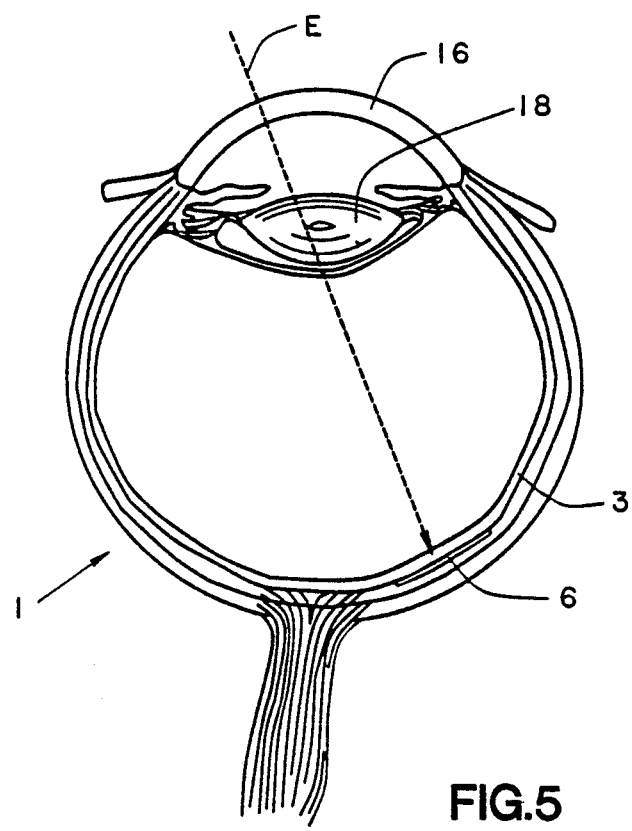
FIG. 5 is a schematic, cross-sectional view of the human eye demonstrating a prior art technique for laser treatment of SRNV.
Figure 6:
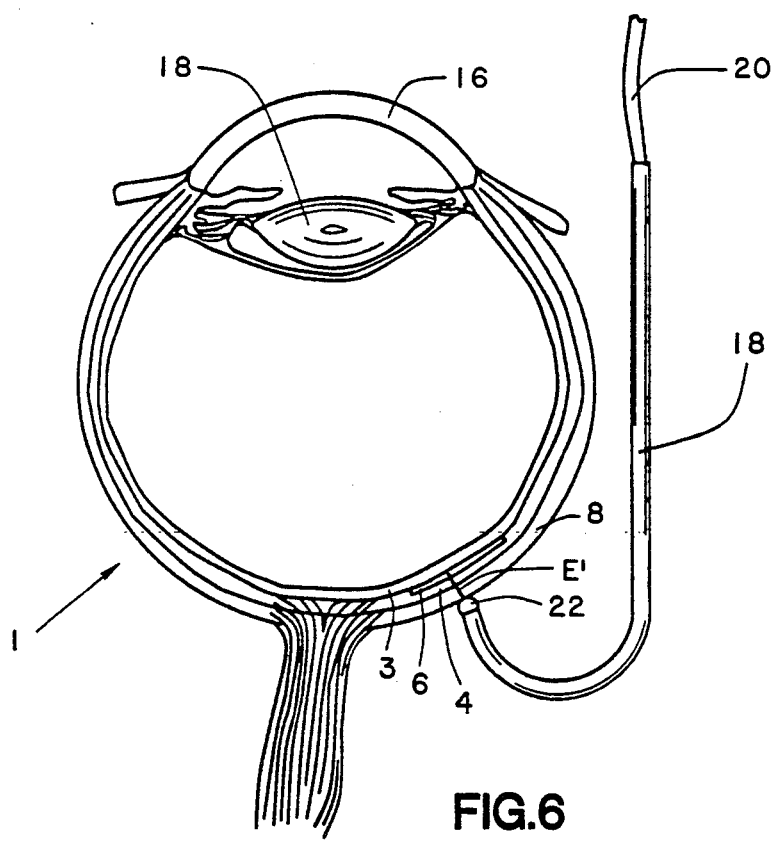
FIG. 6 is a schematic cross-sectional view of the human eye demonstrating the method of the present invention.

The method of the present invention is best illustrated at FIG. 6. A surgeon (not shown) views eyeball 1 through a slit lamp operating microscope, or indirect ophthalmoscope shown generally at 11 in FIG. 3. The surgeon then inserts fiber optic probe 18 behind eyeball 1. In one embodiment of the invention probe 18 is curved as shown. Probe 18 houses fiber optic cable 20 which is attached to laser energy generator 13 (see FIG. 3.). The laser energy generator 13 generates laser energy of a wave length of 1064 NM, for example.

Probe tip 22 is placed against sclera 8 at a point relative to subretinal neovascularization complex 6. The surgeon activates energy generator 13 and laser energy E' is transmitted through sclera 8 and choroid 4 to obliterate subretinal neovascularization complex shown generally at 6.

Probe tip 22 is generally convex and focuses the laser energy approximately 0.5 mm to 2.0 mm from probe tip 22. This allows the energy to be focused in the area of subretinal neovascularization 6. Probe tip 22 can be made of saphire or other appropriate material.

The surgeon continues to view the internal portion of eyeball 1 through slit lamp, operating microscope, or indirect ophthalmoscope 11 and continues to apply laser energy E' until the subretinal neovascularization complex 6 is completely obliterated. Upon complete obliteration of subretinal neovascularization complex 6, laser probe 18 is withdrawn from behind eyeball 1.

As apparent, the method of the present invention can provide obliteration of a subretinal neovascularization complex by using a contact laser, transmitting energy across the sclera and choroid without damaging the retina, thereby eliminating the possibility of retinal damage and visual impairment.

As various changes in the above method could be made without departing from the scope of the invention, it is intended that all matter contained in the above description or shown in the accompanying drawings be interpreted as illustrative and not in a limiting sense.

Having thus described the invention, what is claimed and desired to be secured by letters patent is:

1. A method for treating subretinal neovascular disease with a laser comprising:
   anesthetizing the eyeball;
   preparing the surgical field;
   introducing a fiberoptic probe behind the eyeball;
   visualizing the subretinal neovascular complex through one of a slit lamp, operating microscope, or indirect ophthalmoscope;
   positioning the probe tip relative to the subretinal neovascular complex;
   activating the laser energy;
   focusing the laser energy on the subretinal neovascular complex;
   obliterating the subretinal neovascular complex with the laser energy; and
   withdrawing the fiberoptic probe from behind the patient's eye.

2. The method of claim 1 wherein the fiberoptic probe is curved in shape thereby allowing the placing of the probe tip behind the posterior sclera.

3. The method of claim 1 wherein placing the fiberoptic probe behind the eyeball further comprises placing the fiberoptic probe tip in contact with the sclera.

4. The method of claim 2 wherein placing the fiberoptic probe further comprises placing a quartz fiberoptic probe for transmitting laser energy.

5. The method of claim 1 wherein activating laser energy further comprises the activating laser energy of a wave-length sufficient to be transmitted by the sclera.

6. The method of claim 5 wherein the wave length transmitted by the sclera further comprises emitting a wave length approximately 1064 NM.

7. The method of claim 1 wherein the fiberoptic laser probe tip is convexed and semi-circular for delivering the energy transsclerally.

8. The method of claim 7 wherein the fiberoptic probe tip further comprises a saphire tip for delivering energy transsclerally.

9. A method for photocoagulating subretinal neovascularization comprising:
   preparing the eyeball for the procedure;
   introducing a fiberoptic probe behind the eyeball;
   visualizing the subretinal neovascular complex through one of a slit lamp, operating microscope, or indirect ophthalmoscope;
   placing the fiberoptic probe tip against the sclera relative to the subretinal neovascular complex;
   activating the laser;
   concentrating the laser energy on the subretinal neovascular complex;
   obliterating the subretinal neovascular complex with laser energy; and
   withdrawing the laser probe from the patient.

10. The method of claim 9 wherein the placing of the probe tip against the sclera further comprises the placing of a convex, saphire tip.

11. The method of claim 9 wherein the activating of the laser energy further comprises activating laser energy of a wave length of approximately 1065 NM.

12. The method of claim 9 wherein the introducing of the fiberoptic probe further comprises introducing a quartz fiberoptic bearing probe.

* * * * *